(12) United States Patent
de Vries et al.

(10) Patent No.: US 9,439,584 B1
(45) Date of Patent: Sep. 13, 2016

(54) MOBILE HEALTH DEVICE AND METHOD FOR DETERMINING PATIENT TERRITORY AS A DIGITAL BIOMARKER WHILE PRESERVING PATIENT PRIVACY

(71) Applicant: Medidata Solutions, Inc., New York, NY (US)

(72) Inventors: Glen de Vries, New York, NY (US); Barbara Elashoff, Hillsborough, CA (US)

(73) Assignee: Medidata Solutions, Inc., New York, NY (US)

( * ) Notice: Subject to any disclaimer, the term of this patent is extended or adjusted under 35 U.S.C. 154(b) by 0 days.

(21) Appl. No.: 14/954,021

(22) Filed: Nov. 30, 2015

(51) Int. Cl.
*A61B 5/00* (2006.01)
*A61B 5/11* (2006.01)

(52) U.S. Cl.
CPC .......... *A61B 5/1112* (2013.01); *A61B 5/0022* (2013.01); *A61B 5/6898* (2013.01); *A61B 5/7278* (2013.01)

(58) Field of Classification Search
CPC combination set(s) only.
See application file for complete search history.

(56) References Cited

U.S. PATENT DOCUMENTS

| | | | | |
|---|---|---|---|---|
| 9,338,622 B2* | 5/2016 | Bjontegard | ............ | H04W 4/185 |
| 2008/0143516 A1* | 6/2008 | Mock | .................... | G01S 5/0294 |
| | | | | 340/539.14 |
| 2010/0198608 A1* | 8/2010 | Kaboff | .................... | G06Q 10/00 |
| | | | | 705/2 |
| 2014/0171039 A1* | 6/2014 | Bjontegard | ....... | H04L 29/06034 |
| | | | | 455/414.1 |
| 2015/0262208 A1* | 9/2015 | Bjontegard | ........ | G06Q 30/0202 |
| | | | | 705/7.31 |
| 2016/0007934 A1* | 1/2016 | Arnold | ................. | A61B 5/1123 |
| | | | | 600/595 |

* cited by examiner

*Primary Examiner* — Thomas Tarcza
*Assistant Examiner* — Edward J Pipala
(74) *Attorney, Agent, or Firm* — Steptoe & Johnson LLP; Robert Greenfeld (57) ABSTRACT

Devices and methods are disclosed for use and processing of patient geolocation data in order to objectively determine a patient's territory as an artificially created digital biomarker while maintaining locational privacy. The objective determination of a patient's territory, defined as the area traversed in a specific time interval, can be used as a measurement of quality of life, as well as socio-economic contribution and benefit. Devices and methods are also disclosed for creating an artificial Overall Territory Activity Digital Biomarker based on Patient Activity Factors in addition to the Patient Territory Digital Biomarker, and which Overall Territory Activity Digital Biomarker also maintains locational data privacy. Furthermore, devices and methods are disclosed for capturing and transmitting digital biospecimens, the transformed geolocation data used to determine the Patient Territory Digital Biomarker. The digital biospecimen data can be subsequently used to create alternative, data privacy-preserving determinations of Patient Territory Digital Biomarkers, Patient Activity Factors, and/or Overall Territory Activity Digital Biomarkers.

15 Claims, 3 Drawing Sheets

MOBILE HEALTH DEVICE AND METHOD FOR DETERMINING PATIENT TERRITORY AS A DIGITAL BIOMARKER WHILE PRESERVING PATIENT PRIVACY

BACKGROUND

Mobile health devices (referred to herein as "mHealth" devices) utilizing geolocation-enabled technology, including cellphones, smart watches and activity or fitness trackers, may generate user geolocation data via Global Positioning System (GPS) or other means (such as Wi-Fi or beacons). mHealth devices may also use one or more sensors or biosensors for measuring physical activity via one or more personal metrics, such as heart rate, respiratory rate, blood pressure, body or skin temperature, body mass, and motion (speed, distance traveled, number of steps taken). mHealth devices may be consumer- and/or medical-grade devices or cellphones executing an application (an "app") in communication with a network-based (cloud-based) application.

However, geolocation data generated by mHealth devices (e.g., GPS coordinates) are identifiable to the user or patient wearing the mHealth device, which renders mHealth devices disadvantageous for many purposes, including adherence to data privacy laws and regulations. In particular, personally identifiable geolocation data are disadvantageous for use in a clinical trial when the person or organization conducting the research (the sponsor or contract research organization (CRO)) does not desire to receive, or is prevented by regulation from receiving, personally identifiable geolocation data.

SUMMARY OF THE DISCLOSURE

The present disclosure describes devices and methods for using and processing patient geolocation data to objectively determine a patient's territory as an artificially created digital biomarker, while maintaining the patient's locational privacy. The objective determination of a patient's territory (the "Patient Territory Digital Biomarker" as described herein), defined as the area the patient traverses in a specific time interval, can be used to measure quality of life, as well as socio-economic contribution and benefit. Because geolocation data (i.e., latitude and longitude coordinates, or latitude, longitude and altitude coordinates) can be excluded in the determination of the Patient Territory Digital Biomarker, patient privacy is maintained, making the Patient Territory Digital Biomarker a suitable measure for general clinical practice and non-regulated clinical research, as well for clinical studies subject to regulations requiring that patients not be identifiable by the sponsor or CRO.

The present disclosure also describes devices and methods for determining an artificially created "Overall Territory Activity Digital Biomarker" based on "Patient Activity Factors" and on the Patient Territory Digital Biomarker, and which Overall Territory Activity Digital Biomarker also maintains locational patient privacy. Furthermore, the present disclosure describes devices and methods for creating and transmitting digital biospecimens, the transformed geolocation data used to determine the Patient Territory Digital Biomarker and the Patient Activity Factors. Digital biospecimens can be subsequently used to create alternative, data privacy-preserving determinations of Patient Territory Digital Biomarkers, Patient Activity Factors, and/or Overall Territory Activity Digital Biomarkers.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

Patients (also known as "subjects" in the context of clinical trials) may use one or more mobile health devices (mHealth devices) or other wearable devices, including cellphone-based apps (any of which are referred to herein as "mHealth devices"), having sensors that monitor physical activity, which is reflected in personal data or metrics such as heart rate, respiratory rate, blood pressure, distance traveled, number of steps taken, etc. However, the variety of data and metrics (e.g., steps taken, heart rate, etc.) generated by different mHealth devices may not be suitably comparable for study purposes, including clinical trial or clinical practice purposes. Moreover, mHealth devices do not objectively capture or determine a patient's territory, that is, the surface area (or volume) that a patient traverses in a specific period of time. Nor do mHealth devices take into account whether such traversal is self-propelled (e.g., walking or running) or assisted (e.g., in a car or train), nor do they limit such territory to only unique area (or volume) traversed. Objective determination of a patient's territory, or a patient's territory together with certain activity within that territory (as defined further herein), may be indicative of disease or therapy progression, quality-of-life changes, and adverse events, and thus may be valuable for clinical trial purposes, including adding value to more traditional, but subjective, clinical endpoints such as pain, shortness of breath, muscle stiffness, fatigue, dizziness, mood, or social interaction. Such objective determinations may also be valuable for clinical practice and for research such as Real World Evidence (RWE) or Post-Marketing Surveillance (PMS) trials.

Currently, if considered at all, a patient's activity (in particular mobility, e.g., an ability to travel outside of a room or a home, average self-propelled speed, ability to travel in vehicles, and other indications of capacity to participate in society) is qualitative, and either subjectively determined and recorded by the patient (e.g., via patient-reported outcomes or a patient diary) or is subjectively observed and recorded by a health professional, which requires an inpatient setting and is therefore an uncommon and limiting practice. Patients often do not accurately record information concerning their activity, and the self-reported nature of traditional patient-reported outcomes (PRO) inherently introduces the potential for biases (recall bias, etc.), due to the subjective view of the patient. Any reporting of patient activity or mobility that is left to the subjective experience and recollection of a patient includes a likelihood of misreporting (non-reporting or incomplete or inaccurate reporting). Even when objectively recorded by a clinician or when objectively self-recorded by a patient, for example with a six-minute walk test (which is a measure only of movement potential), the data is both episodic in nature and does not reflect the patient's full daily movement patterns.

The present disclosure describes devices and methods for further processing, use, and the prevention of further transmission of mHealth geolocation data in order to objectively determine a Patient Territory Digital Biomarker suitable for purposes of clinical study quality-of-life endpoints, socio-economic studies, and clinical practice, while also preserving patient privacy. The determined Patient Territory Digital Biomarker may take into account assisted mobility and self-propelled mobility. The disclosure also describes devices and methods for determining an Overall Territory Activity Digital Biomarker that is based on the Patient Territory Digital Biomarker and Patient Activity Factors, each of which may include a determination of assisted mobility (all described further herein), while preventing transmission of locational data. The disclosure also describes devices and methods for determining, transmitting and using digital biospecimens while preventing transmission of locational data to preserve patient privacy.

The determined Patient Territory Digital Biomarker may thus be used in clinical trials, clinical practice or other research, based on the objective determination of a patient's patterns of movement, or a Patient Territory Digital Biomarker together with certain concurrent patient activity patterns. In contrast to "natural" or non-digital biomarkers, which are measurable aspects of an organism indicative of a disease of condition (e.g., certain antibodies that indicate infections, or rubidium chloride to indicate perfusion of cardiac muscle). A Patient Territory Digital Biomarker as described herein is an artificially determined, objective, digital indication of a patient's disease or condition based on mHealth device-derived patient geolocation data. The Patient Territory Digital Biomarker as described herein is an objective digital measurement that can be used as a surrogate marker for a patient's disease progression or overall health using patient-attached or wearable technologies (mHealth devices) that provide granular geolocation data concerning the patient. The devices and related methods described herein use geolocation data from mHealth devices (including cellphone-based apps) in order to determine the Patient Territory and Overall Territory Activity Digital Biomarkers, while at the same time preventing access to geolocation data by the parties conducting research or otherwise monitoring a patient, thus preserving the patient's privacy. The device may operate in real-time or have one or more uploads of data. The device is both objective and deterministic, meaning that identical patient behavior will result in substantially the same measurement, making it a particularly useful marker for clinical insights in the efficacy of various therapies, devices or other medical or social interventions. The determinations may also be used to assess socio-economic value, in a way that is appropriate for determining the reimbursable value of different treatments. Because of the privacy-preserving nature of the device, it is also appropriate for use in regulated clinical trials. Furthermore, the nature of the mechanism used to determine Patient Territory Digital Biomarkers is non-invasive and can be performed with devices that the patient already uses for other purposes (for example, a smartphone) to reduce the burden on patients participating in research.

The devices and methods described herein generate and transform a patient's mHealth device-derived geolocation data to determine an objective measure of a patient's territory while preserving patient locational privacy. The devices or methods may generate patient geolocation data in one or multiple data sources, including cellphones or mHealth devices enabled with GPS and/or Wi-Fi, or enabled with signals from radio beacons. The geolocation data may be generated over configurable sampling intervals, that is, at intervals (4×/minute, 1×/minute, etc.) equal to or greater than the interval for which data are otherwise available from the patient's mHealth device. For example, an mHealth device may generate and provide geolocation data once or more per second, but the device may aggregate several of those intervals and report data every five seconds, or twice a minute, etc. Geolocation data generated over such sampling intervals may be transformed, using vector-based calculations, closest-fit geometric calculations, or other suitable algorithms, to determine Patient Territory Digital Biomarkers and the Patient Activity Factors which, in turn, may be used to determine an Overall Territory Activity Digital Biomarker. As described further herein, the Patient Territory Digital Biomarker and Patient Activity Factors, once determined over the configured sampling intervals, may also be further calculated over grouped or summed intervals, such as a day, as well as longer intervals, such as a week or a month.

As discussed herein, a patient's assisted mobility (or its converse, self-propelled mobility) may be determined or estimated by the present invention. The Patient Territory Digital Biomarker and the Patient Activity Factors used in the Overall Territory Activity Digital Biomarker may take into account (include, exclude, or weight somewhere in between) assisted mobility. In some embodiments, the results of initial calculations (i.e., the vectors, or distances and degrees resulting from operation 320, described with reference to FIG. 3, below) based on geolocation data may also be captured, transmitted and stored as digital biospecimens. In contrast to "natural" or non-digital biospecimens, which are physical samples taken from an organism for purposes of later diagnosis or analysis, digital biospecimens are artificially determined, de-identified data based on patient geolocation data (the results of operation 320) prior to conversion to Patient Territory Digital Biomarkers or Overall Territory Activity Digital Biomarkers. Digital biospecimens may be used to later reconstitute or re-determine Patient Territory Digital Biomarkers, Patient Activity Factors, and/or Overall Territory Activity Digital Biomarkers while also preserving patients' locational data privacy.

Figure 1:
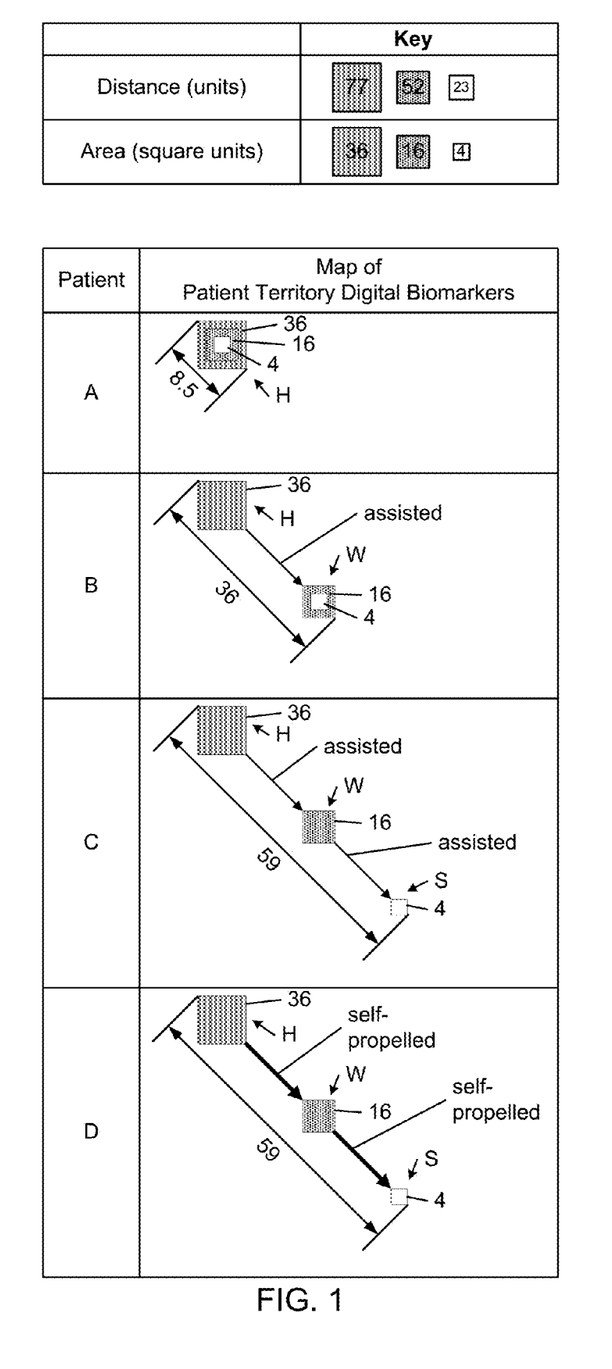
FIG. 1 illustrates comparative Patient Territory Digital Biomarkers, as may be determined by embodiments of the present invention.

Non-limiting embodiments of the determination of Patient Territory Digital Biomarkers and Patient Activity Factors are illustrated with reference to FIG. 1 and Table 1, in which a Patient Territory Digital Biomarker and specific Patient Activity Factors (labeled as "Distance," "Furthest Point" and "Speed") are calculated for four patients, Patients A, B, C and D. As illustrated in FIG. 1, the Patient Territory Digital Biomarker is the sum of the areas (or, in some embodiments, taking into account altitude differences, may be the sum of the volumes) that a patient traverses in a certain period of time. Each of the four patients has three periods of activity (physical movement) during one day in which each traverses at least some area; those areas as shown in FIG. 1 are 36 square units, 16 square units, and 4 square units. Though Patient A has three periods of activity (described further herein) in one day, all three are in one place (e.g., at home), and as a result, each of the areas overlaps so that Patient A's Patient Territory Digital Biomarker corresponds to the area of the largest unique movement, which is 36 square units. (As shown in FIG. 1, 36 square units is the area of the 6 by 6 square; however, had Patient A traversed a subset of that square, the corresponding Patient Territory Digital Biomarker would be less than 36 units.) In contrast, while Patient B also traverses the same areas (36, 16 and 4 square units) in each of three periods of activity, two of those areas are at a different location (e.g., the first period of activity is at home, the second two are at work), and as a result Patient B's Patient Territory Digital Biomarker is 52 square units. Similarly, because the area traversed during each of Patient C's three periods of activity occurs in three different locations (e.g., at home, at work, and at a store), Patient C's Patient Territory Digital Biomarker is somewhat greater, 56 square units. Patient D's Patient Territory Digital Biomarker takes into account her self-propelled movement (discussed below) between the locations at which Patient D moves, and thus is greater, 98 square units. In total, within the period of one day, Patient A has the smallest Patient Territory Digital Biomarker (36 square units); Patients B and C have similar Patient Territory Digital Biomarkers that are appreciably greater (52 and 56 square units, respectively) than that of Patient A; and Patient D has the largest Patient Territory Digital Biomarker (98 square units), which is appreciably greater than that of the other patients. (Patient Territory Digital Biomarker values may also be normalized to provide a value between 0 and 1. Methods for determining a Patient Territory Digital Biomarker are discussed further with regard to FIG. 3.)

TABLE 1

| Patients (Description of Activity) | Patient Territory Digital Biomarker | Patient Activity Factors | | |
|---|---|---|---|---|
| | | Distance | Furthest Point | Speed (m/s) |
| Patient A (3 periods of activity in 1 day; all 3 are at the same location) | 36 square units | 77 + 52 + 23 = 152 units | 8.5 units | 0.266 |
| Patient B (3 periods of activity in 1 day; the first at a first location, the second two at a second location; movement between the locations is assisted) | 36 + 16 = 52 square units | 77 + 52 + 23 = 152 units | 8.5 + 22 + 5.5 = 36 units | 0.333 |
| Patient C (3 periods of activity in 1 day, each at a different location; movement between each location is assisted) | 36 + 16 + 4 = 56 square units | 77 + 52 + 23 = 152 units | 8.5 + 22 + 5.5 + 20 + 3 = 59 units | 1.0 |
| Patient D (3 periods of activity in 1 day, each is at a different location; movement between each location is self-propelled) | 36 + 16 + 4 + 22 + 20 = 98 square units | 77 + 52 + 23 + 22 = 20 = 194 units | 8.5 + 22 + 5.5 + 20 + 3 = 59 units | 0.94 |

With reference to FIG. 1 and Table 1, one or more Patient Activity Factors may be calculated and used, in addition to the Patient Territory Digital Biomarker, to determine an Overall Territory Activity Digital Biomarker. The Distance Patient Activity Factor is the overall distance traversed by a patient during a period of activity, and as provided in the example in FIG. 1 and Table 1, is 77 units for the first period of activity, 52 units for the second period of activity, and 23 units for the third period of activity. The Furthest Point Patient Activity Factor is the longest absolute distance traversed by a patient within a period of activity, and as the example in FIG. 1 and Table 1 shows, is 8.5 units for Patient A, 36 units for Patient B, and 59 units for Patients C and D. The Speed Patient Activity Factor is the average speed of the patient's movement during a period of activity, and as provided for in the example in FIG. 1 and Table 1, is 0.266 meters per second for Patient A, 0.333 meters per second for Patient B, 1.0 meters per second for Patient C, and 0.944 meters per second for Patient D. (The values for Distance and Speed provided in FIG. 1 and Table 1 are not directly related to the Patient Territory Digital Biomarkers values. The Speed and Distance values for Patients A through D may vary where patients traverse a greater or lesser overall distance at greater or lower speeds within each of the corresponding periods of activity, without changing the values of the Patient Territory Digital Biomarkers. As discussed herein, Patient Territory Digital Biomarkers and Patient Activity Factors are based on the results of operation 320 via vector-based calculations.)

The determined Patient Activity Factors thus illustrate significant differences between Patients A through D that can be reflected in the determination of an Overall Territory Activity Digital Biomarker. For example, while Patients B and C have similar Patient Territory Digital Biomarkers (and identical Distance Patient Activity Factors), determination of their other respective Patient Activity Factors reveals that Patient C has significantly greater Furthest Point (59 versus 36 units, respectively) and Speed (1.0 m/s versus 0.333 m/s, respectively). In contrast, and as a further example, while Patient D's Patient Territory Digital Biomarker is significantly greater than Patient C's (98 versus 56 square units), and while Patient D's Distance is significantly greater than Patient C's (194 units versus 152 units), the Furthest Point for both patients is the same (50 units) and the Speed for both patients is similar (0.94 m/s and 1.0 m/s, for Patients D and C, respectively). The differences in Patient Territory Digital Biomarkers and Patient Activity Factors may indicate, for example, that Patient D participates in more social activity than Patient C, or that Patient D works while Patient C is unable to work.

Further, the Speed Patient Activity Factor for each of the Patients in Table 1 may be determined as an average speed for each period of activity of a patient's movement over the corresponding sampling interval(s) (described above) or as the average speed across grouped or summed intervals (which would include periods of activity). In some embodiments, such determinations may be calculated for only self-propelled mobility (discussed further with reference to FIG. 3). For example, the fact that Patients B and C drove and were not self-propelled over the distance between their periods of activities may be used to discount their Distance Patient Activity Factor. As shown in Table 1, the Distance Patient Activity Factor for Patients B and C does not include the distances traversed between their respective periods of activity. As also shown in Table 1, Speed for Patients B and C entirely discounts their speed over those distances, i.e., Speed is determined only with respect to their self-propelled movements during the three periods of activity and not between them. Patient D's Speed is calculated as 0.94 m/s, and reflects that Patient D likely walked, i.e., was self-propelled, over all distances including the distances between her three periods of activity.

While the speeds for distances between areas of activity that are not self-propelled (e.g., travel by car, plane, etc.) for Patients B and C are not reflected in the Speed calculations, other embodiments (described further below) may take into account such non-self-propelled speed or activity (i.e., assisted mobility) as part of an Overall Territory Activity Digital Biomarker. A capacity for one or more trips via car, bus, plane, etc. over a summed or grouped interval (day, week, month, etc.) may reflect a higher quality of life than a patient who, though active or mobile as reflected by the Patient Territory Digital Biomarker, is otherwise unable to take such trips.

FIG. 1 and Table 1 thus illustrate that an Overall Territory Activity Digital Biomarker may take into account a Patient Territory Digital Biomarker and one or more Patient Activity Factors, which in turn may take into account assisted mobility (or its converse, self-propelled mobility). An Overall Territory Activity Digital Biomarker may constitute a quality-of-life clinical endpoint, or even a clinical objective, and be valuable for clinical trial purposes as well as for diagnosis and treatment in clinical practice. It will be appreciated that each of the Patient Activity Factors calculated with regard to comparing Patients A, B, C, and D may also be used to provide objective comparisons of the same patient over different periods of time (e.g., grouped or summed intervals). It will also be appreciated that the relative importance of each of the Patient Activity Factors may be determined by the clinical researcher or the doctor, based on the respective research or clinical interests, as well as on the patient's wishes, therapy, and/or disease. For example, if a clinical trial is studying the disease of social anxiety, then Distance and Furthest Point, but not Speed, may be weighted more heavily to reflect their importance. If a clinical trial is studying Muscular Dystrophy, then Speed may be weighted as more important than Furthest Point and Distance. Further, the examples illustrated in FIG. 1 and Table 1 provide objective and comparable digital biomarker determinations even where the patients have a different or unequal number of periods of activity, provided that identical overall periods of time (that is, the total of the grouped or summed intervals, which may be days, weeks, etc.) are used.

As stated above, an Overall Territory Activity Digital Biomarker may be calculated based on one or more Patient Activity Factors and the Patient Territory Digital Biomarker. An example of this is the formula:

$$y = T + a(D + FP + S) \quad \text{(Eq. 1)}$$

where T is the Patient Territory Digital Biomarker, a is a coefficient between 0 and 1, and D, FP and S are the Distance, Furthest Point and Speed Patient Activity Factors, respectively. The coefficient a can be a measure of the overall weight of the Patient Activity Factors relative to the Patient Territory Digital Biomarker in the determination of an Overall Territory Activity Digital Biomarker. For example, with a=0.2 and using the values provided in Table 1, the Overall Territory Activity Digital Biomarkers for Patients A, B, C and D are approximately 68, 90, 98 and 147, respectively. Where a=0.5, the overall territory activity digital biomarkers are approximately 116, 146, 162 and 225, respectively. In addition, the resulting Overall Territory Activity Digital Biomarkers may be normalized to provide a value between 0 and 1, where 0 represents an immobile patient and 1 represents a mobile patient. A user of the device described herein may configure the exact coefficient in the above linear equation, because as noted, different coefficients may prove useful in different clinical contexts, for example in different therapeutic areas (e.g., oncology versus cardiology).

In another embodiment, separate coefficients from 0 to 1 may be configured for each Patient Activity Factor. For example, an Overall Territory Activity Digital Biomarker may be calculated by using the formula:

$$y = T + bD + cFP + dS \quad \text{(Eq. 2)}$$

where T is the Patient Territory Digital Biomarker, b, c, and d are coefficients between 0 and 1, and D, FP and S are the Distance, Furthest Point and Speed Patient Activity Factors, respectively. As an example, where the coefficients are b=0.8, c=0 and d=0.3, in order to provide weight for the Distance and Speed Patient Activity Factors while entirely discounting the Furthest Point Patient Activity Factor (e.g., to discount the impact of travel such as a long plane trip, where the therapeutic area under study would minimize or exclude that factor), the Overall Territory Activity Digital Biomarkers for Patients A, B, C and D are approximately 157, 174, 178 and 254, respectively. Stored digital biospecimens, discussed herein, provide the necessary data to calculate the optimal coefficients for different therapeutic use cases and may also provide necessary data for observational studies or control studies.

The individual coefficients may also be used to reflect periods of assisted mobility. For example (and using the indications provided by operation 340, discussed below), for periods of activity in which there is assisted mobility, coefficients may be set to 0, entirely discounting the Distance, Furthest Point and/or Speed Patient Activity Factors for those periods. Conversely, coefficients for the Patient Activity Factors in the above formulas (Equations 1 and 2) may be set between 0 and 1 to indicate a discount, and may be set to 1 to reflect self-propelled mobility to provide a full weight for the Patient Activity Factors in the determination of an Overall Territory Activity Digital Biomarker.

In other embodiments of the present invention, an Overall Territory Activity Digital Biomarker may be calculated by using formulas that account for assisted mobility without use of the indications provided by operation 345. For example, an Overall Territory Activity Digital Biomarker may be calculated by using either of the formulas $$y = T + (T*S)*((\ln(FP) + D)/2) \quad \text{(Eq. 3)}$$

$$y = T + (T*(ln(FP) + (S*D))) \quad \text{(Eq. 4)}$$

where T is the Patient Territory Digital Biomarker, and D, FP and S are the Distance, Furthest Point and Speed Patient Activity Factors, respectively. The following tables provide values to illustrate the operation of the above formulas for new Patients E through V (not shown in FIG. 1).

TABLE 2A

| Patients | Patient Territory Digital Biomarker | Distance | Furthest Point | Speed (m/s) | Overall Territory Activity Digital Biomarker (Eq. 3) | Overall Territory Activity Digital Biomarker (Eq. 4) |
|---|---|---|---|---|---|---|
| E | 10 | 100 | 10000 | 0.25 | 147 | 352 |
| F | 20 | 100 | 10000 | 0.25 | 293 | 704 |
| G | 40 | 100 | 10000 | 0.25 | 586 | 1408 |
| H | 20 | 100 | 10000 | 0.25 | 293 | 704 |
| I | 20 | 100 | 10000 | 0.5 | 566 | 1204 |
| J | 20 | 100 | 10000 | 1.0 | 1112 | 2204 |
| K | 20 | 50 | 10000 | 0.25 | 168 | 454 |
| L | 20 | 100 | 10000 | 0.25 | 293 | 704 |
| M | 20 | 200 | 10000 | 0.25 | 543 | 1204 |

TABLE 2B

| Patients | Patient Territory Digital Biomarker | Distance | Furthest Point | Speed (m/s) | Overall Territory Activity Digital Biomarker (Eq. 3) | Overall Territory Activity Digital Biomarker (Eq. 4) |
|---|---|---|---|---|---|---|
| N | 10 | 100 | 50 | 0.25 | 140 | 299 |
| O | 20 | 100 | 50 | 0.25 | 280 | 598 |
| P | 40 | 100 | 50 | 0.25 | 560 | 1196 |
| Q | 20 | 100 | 50 | 0.25 | 280 | 598 |
| R | 20 | 100 | 50 | 0.5 | 540 | 1098 |
| S | 20 | 100 | 50 | 1.0 | 1059 | 2098 |
| T | 20 | 50 | 50 | 0.25 | 155 | 348 |
| U | 20 | 100 | 50 | 0.25 | 280 | 598 |
| V | 20 | 200 | 50 | 0.25 | 530 | 1098 |

There are several aspects to be appreciated with regard to Equations 3 and 4. First, Table 2A illustrates the situation in which a patient (e.g., Patients E through M) has traveled in some assisted manner, e.g., a long plane ride, and each has a Furthest Point of 10,000. Within Table 2A, one Patient Activity Factor (or the Patient Territory Digital Biomarker) other than Furthest Point is varied at a time: the Patient Territory Digital Biomarker is doubled for each of Patients E, F and G; Speed is doubled for each of Patients H, I and J; and Distance is doubled for each of Patients K, L and M. In contrast, Table 2B illustrates the situation in which a patient (Patients N through V) has traveled under his or her own power, e.g., with self-propelled mobility, has stayed within the same town, and each has a Furthest Point of 50. Within Table 2B, just as for Table 2A, one Patient Activity Factor (or the Patient Territory Digital Biomarker) is varied at a time: the Patient Territory Digital Biomarker is doubled for each of Patients N, O and P; Speed is doubled for each of Patients Q, R and S; and Distance is doubled for each of Patients T, U and V.

The resulting Overall Territory Activity Digital Biomarkers reflect the impact of Furthest Point in each of the equations. With regard to Equation 3, comparing the Patients in Tables 2A and 2B (e.g., comparing Patient E to Patient N, Patient F to Patient O, etc.), the Overall Territory Activity Digital Biomarkers for each patient in Table 2A are consistently approximately 3% to 8% higher than those in Table 2B. It will also be appreciated that an increase in one of the other Patient Activity Factors (Speed or Distance) results in a diminished increase in Overall Territory Activity Digital Biomarker value. Specifically, the doubling of Speed (compare the values for Patients H, I and J or Patients Q, R, and S to each other) results in less than a doubling of the resulting Overall Territory Activity Digital Biomarker. Similarly, the doubling of the Distance Patient Activity Factor results in less than a doubling of the resulting Overall Territory Activity Digital Biomarker (compare Patients K, L and M or Patients T, U and V). It will also be appreciated that a doubling of the Patient Territory Digital Biomarker does result in an exact doubling of the Overall Territory Activity Digital Biomarker, as seen by comparing Patients E, F and G, or Patients N, O and P, to each other. It thus will be appreciated that Equation 3 (and Equation 4, for which similar comparisons may be made) appropriately balances the impact of the Patient Activity Factors on the Overall Territory Activity Digital Biomarker. In addition, it will be appreciated that the use of the natural log of the Furthest Point in both Equations 3 and 4 provides an appropriate weighting, in that the impact of a very large Furthest Point does not disproportionately affect the Overall Territory Activity Digital Biomarker. A patient in effect is credited with ability to travel in an assisted manner, but her Overall Territory Activity Digital Biomarker is not unduly increased in direct proportion to distance traveled—it is not substantially different for self-propelled mobility, such as self-propelled movement only within a town, as represented in Table 2B, versus assisted mobility, such as travel via an airplane, as represented in Table 2A. The natural log also appropriately takes into account the difference between, for example, a four-hour flight versus a one-hour flight, by appropriately increasing the resulting Overall Territory Activity Digital Biomarker by far less than a factor of four.

With further regard to Equation 4, the resulting Overall Territory Activity Digital Biomarkers using the values provided in Tables 2A and 2B reflect a consistently greater impact of Furthest Point compared with Equation 3. That is, the Overall Territory Activity Digital Biomarkers for each patient in Table 2A using Equation 4 are approximately 5% to 23% higher than those in Table 2B (e.g., comparing Patient E to Patient N, Patient F to Patient O, etc.), whereas the Overall Territory Activity Digital Biomarkers for each patient in Table 2A using Equation 3 are, as noted, approximately 3% to 8% higher than those in Table 2B. It will also be appreciated that, using Equation 4, an increase to one of the other Patient Activity Factors (Speed or Distance) results in a reduced increase to the Overall Territory Activity Digital Biomarker than the Overall Territory Activity Digital Biomarker determined with Equation 3.

Further, in embodiments utilizing digital biospecimens as provided herein, a Patient Territory Digital Biomarker or Overall Territory Activity Digital Biomarker used in a clinical trial may be later reconstructed or recalculated pursuant to a different formula. Such reconstruction may occur when the device is being used in a different research context. It is also possible that certain coefficients may be useful in multiple therapeutic contexts.

Figure 2A:
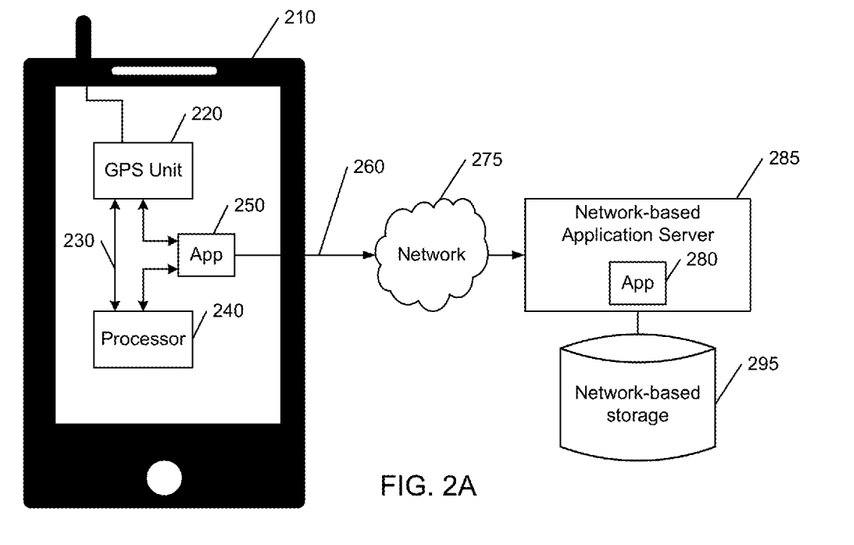
FIGS. 2A and 2B are block diagrams of devices for determining a Patient Territory Digital Biomarker based on, and preventing the transmission of, mHealth-generated geolocation data, according to embodiments of the present invention.

Reference is now made to FIG. 2A, which is a block diagram of a device 210 for determining Patient Territory Digital Biomarkers, Patient Activity Factors, Overall Territory Activity Digital Biomarkers, and digital biospecimens. As shown in FIG. 2A, GPS Unit 220 of a patient's mHealth device 210 may generate geolocation data and corresponding time points 230. GPS Unit 220 is a geolocation coordinate generator that generates geolocation data and corresponding time points 230 by receiving GPS signals from one or more GPS satellites, and/or Wi-Fi signals and/or signals from radio beacon. Geolocation data with corresponding time points 230 may be received regularly, continuously, or irregularly and non-continuously. The resulting geolocation data with corresponding time points 230 may be transformed by the mHealth device's processor 240 executing instructions for vector-based calculations received from mHealth-based application 250 in order to generate vectors (or distances and corresponding degrees) 260. Vector-based calculations include parametric kernel methods, minimum convex polygon (MCP) methods, local convex hull (Lo-CoH) nonparametric kernel methods, or Time Local Convex Hull (T-LoCoH) methods. Vectors 260 may be transmitted via a network 275 to network-based application 280 executing with a processor (not shown) of a network-based application server 285. Network-based application 280 may determine Patient Territory Digital Biomarkers, Patient Activity Factors, and/or Overall Territory Activity Digital Biomarkers (not shown) based on vectors 260 and store those determined values in network-based storage 295.

Figure 2B:
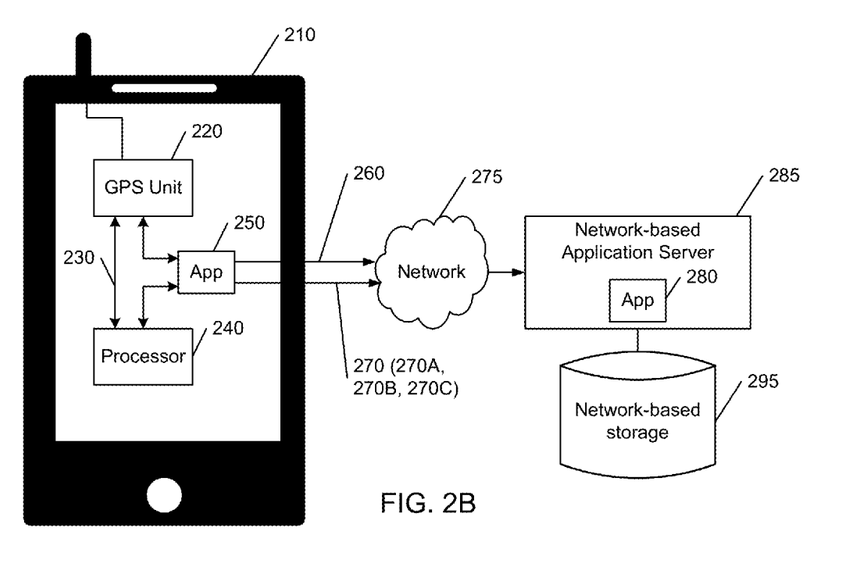

As shown in FIG. 2B, Patient Territory Digital Biomarkers 270A, Patient Activity Factors 270B, and/or Overall Territory Activity Digital Biomarkers 270C (collectively 270) may be determined based on vectors 260 (resulting from the same transformation as described for FIG. 2A), using instructions received from mHealth-based application 250 executing on mHealth device processor 240. It will be appreciated that in contrast to FIG. 2A, the determination of Patient Territory Digital Biomarkers, Patient Activity Factors, and/or Overall Territory Activity Digital Biomarkers 270 is executed by mHealth-based application 250 rather than by network-based application 280. The determined Patient Territory Digital Biomarkers, Patient Activity Factors, and/or Overall Territory Activity Digital Biomarkers 270 may be transmitted via network 275 and via network-based application 280 of a network-based application server 285 to network-based storage 295.

With regard to both FIG. 2A and FIG. 2B, vectors 260 may be transmitted as digital biomarkers via network 275 and via network-based application 280 to network-based storage 295. As discussed herein, digital biospecimens may then be used for alternative determinations of Patient Territory Digital Biomarkers, Patient Activity Factors, and/or Overall Territory Activity Digital Biomarkers executed by network-based application 280 on network-based application server 285. Access to network 275 may be wireless or wired, or a combination, and may be short-range or longer range, via satellite, telephone network, cellular network, Wi-Fi, over other public or private networks, via Ethernet, or over local, wide, or metropolitan area networks (i.e., LANs, WANs, or MANs). Where transmitted via network 275, Patient Territory Digital Biomarkers, Patient Activity Factors, and/or Overall Territory Activity Digital Biomarkers 270 exclude specific geolocation data such as latitude, longitude and altitude, preserving patient locational privacy. The determination of Patient Territory Digital Biomarkers, Patient Activity Factors, and/or Overall Territory Activity Digital Biomarkers in both FIGS. 2A and 2B may be accomplished as described with reference to FIG. 1.

mHealth-based application 250 may also calculate and transmit the number of measurements on which the transformation of vectors 260 was based (a "precision number," not shown) to network-based application server 285 for further processing, such as the determination of a quality score (for example, a digital biomarker may be viewed as more accurate where its precision number is higher). Patient Territory Digital Biomarkers, Patient Activity Factors, and/or Overall Territory Activity Digital Biomarkers from network-based application server 285 may also be transmitted to and processed by other clinical data systems (not shown), including Electronic Data Capture (EDC), and included in the patient's clinical record, e.g., an electronic case report form (eCRF) in the EDC system.

Figure 3:
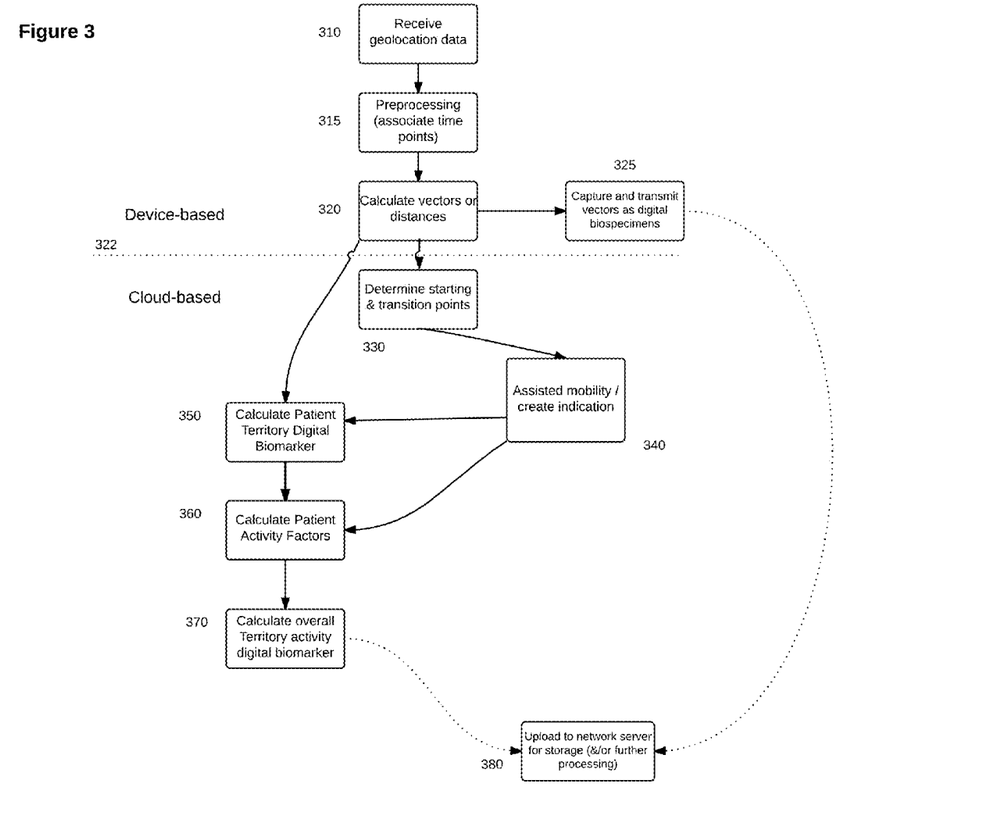
FIG. 3 is a flowchart of a method for determining Patient Territory Digital Biomarkers and Overall Territory Activity Digital Biomarkers, according to embodiments of the present invention.

Reference is now made to FIG. 3, a flowchart illustrating the general operation of a device for determining Patient Territory Digital Biomarkers, Patient Activity Factors, Overall Territory Activity Digital Biomarkers and digital biospecimens. In operation 310, geolocation data (e.g., latitude, longitude, altitude coordinates from a geolocation coordinate generator of a GPS-enabled mHealth device) may be received by an application executing on the mHealth device (mHealth-based application 250). In operation 315, the geolocation data may be pre-processed by mHealth-based application 250, such as converting the GPS coordinates to units in meters, degrees, etc.

In operation 320, mHealth device processor 240 may execute vector-based calculations (discussed herein), including calculating the distance between geolocation coordinates corresponding to two consecutive time points (an interval) or over non-consecutive time points, i.e., a sampling interval. Processor 240 may also calculate both the distance between the geolocation coordinates corresponding to an interval and the direction of that distance as measured in degrees, which together are a vector. The distances and degrees, or vectors, may be calculated for the intervals between the received time points of each of the sampling intervals or may also be calculated as subtotal or total distances and directions (e.g., spanning more than one sampling interval).

Starting points and/or transition points may be determined in operation 330. Starting points and/or transition points may be required for the determination of self-propelled activity and/or assisted mobility (which in turn may be required for the calculation of Patient Territory Digital Biomarkers and Patient Activity Factors). Operation 330 may be performed either on mHealth device 210 or on network-based application server 285. A starting point may be a first interval having a speed value after one or more intervals having very low or no speed values. For example, a first speed value (e.g., 0.95 m/s) for an interval above a configurable threshold value (e.g., 0.1 m/s) may indicate the beginning of patient self-propulsion. Similarly, a transition point may be a first interval or several continuous intervals having a significantly (e.g., order of magnitude, or crossing a threshold) higher or lower speed value than the speed for preceding intervals that indicated patient self-propulsion. For example, a transition point may be determined in which a minimum number of intervals (one or more) have speed values above a configurable threshold indicative of assisted mobility (e.g., above 2.5 m/s), or where speed values jump appreciably, e.g., from 0.5 m/s to 5.0 m/s (an order of magnitude).

Assisted mobility may be determined in operation 340 by using the starting points and/or transition points determined in operation 330. With regard to the eventual calculation of a Patient Territory Digital Biomarker in operation 350 or Patient Activity Factors in operation 360, an indication of assisted mobility may be determined corresponding to the distances between or within periods of activity in which a patient traversed an area. For example, as discussed with reference to FIG. 1, Patient C's movements between the three locations during his periods of activity were assisted and were not included in the determination of his Patient Territory Digital Biomarker; in contrast, Patient D's movements between the three locations during her periods of activity were self-propelled and were included in the determination of her Patient Territory Digital Biomarker and Distance Patient Activity Factor. (In order to calculate a Patient Territory Digital Biomarker for distances traveled between periods of activity, those distances may be assumed to have a single unit in a second dimension, e.g., 1×22 and 1×18 for Patient D's Patient Territory Digital Biomarker as shown in Table 1).

An indication of assisted mobility may also be created in operation 340 for those intervals (e.g., subsequent to a starting point and prior to a transition point) for which a speed is below a range (e.g., less than 1.5 m/s) that likely corresponds to self-propelled mobility. An indication of self-propelled mobility may be applied to one or more of overall distance (for determination of a Distance Patient Activity Factor), total or absolute Distance (for determination of a Furthest Point Patient Activity Factor), and average speed (for determination of a Speed Patient Activity Factor). For any intervals having speeds within a subsequent range (e.g., between 1.5 m/s and 2.5 m/s) where patient mobility is not clearly assisted or self-propelled, an indication to apply a discount (e.g., 50%) may be created and then applied to the Distance, Furthest Point, and/or Speed Patient Activity Factors for those intervals. Similarly, for any intervals having speeds above a subsequent range (e.g., >2.5 m/s) where movement is very likely to be assisted, an indication may be created for a total discount to be applied to the Distance, Furthest Point, and/or Speed Patient Activity Factors for those intervals. In some embodiments, as discussed above with reference to FIG. 1, where a patient's movement over those intervals is likely assisted (e.g., via a vehicle), determination of the Overall Territory Activity Digital Biomarker may thereby take such assisted mobility into account. Other or additional gradations of the determination of patient self-propulsion than the three ranges described herein with regard to operation 340 may be calculated applying appropriate discounts to those gradations. The ranges described above may be configurable by a user of the device through an interface to mHealth-based application 250 or to network-based application 280 in communication with the mHealth application.

The indications of assisted mobility discussed above may also be applied as coefficients in the formulas provided herein for determining Overall Territory Activity Digital Biomarkers, specifically as coefficients in those formulas for Patient Activity Factors. As noted above, a formula may also sufficiently account for self-propelled mobility or assisted mobility, described with regard to the natural log function in Equations 3 and 4.

In operation 350, Patient Territory Digital Biomarkers may be calculated using the indications created in operation 340. For example, as noted with regard to operation 330, Patient C's movement between the three locations during his periods of activity are assisted mobility and may be excluded in the determination of his Patient Territory Digital Biomarker, while Patient D's movement between the three locations during her periods of activity are self-propelled and may be included in the determination of her Patient Territory Digital Biomarker. As a Patient Territory Digital Biomarker is defined as the area a patient traverses in a specific period of time, the indications created in operation 340 may be applied to any time intervals between a starting point and a transition point or between two transition points, or may be applied to each period of activity.

The Patient Territory Digital Biomarker calculations in operation 350 may be executed on mHealth device 210 or, after transmission via network 275, may be executed on network-based application server 285 (e.g., in the "cloud") using the above-described vectors in vector-based calculations (as noted above, these include parametric kernel methods, minimum convex polygon (MCP) methods, local convex hull (LoCoH) nonparametric kernel methods, or Time Local Convex Hull (T-LoCoH) methods). The vector-based calculations may be stored in mHealth-based application 250 or in network-based application 280. Vector-based calculations for the determination of Patient Territory Digital Biomarkers may be computationally complex algorithms or formulas and so may be more appropriately executed on network-based application server 285 to reduce the processing burden on mHealth device processor 240. As discussed above with reference to FIG. 1, the Patient Territory Digital Biomarker may be determined based on vectors and corresponding time points across grouped or summed intervals (e.g., across multiple sampling intervals), such as a day, as well as longer intervals, such as a week or a month.

As also illustrated in FIG. 3, the results—the distances and degrees, or vectors 260—of the vector-based calculations in operation 320 may be captured and transmitted in operation 325 as digital biospecimens. The digital biospecimens may be received and stored in cloud-based storage (e.g., network-based storage 295) in operation 380 any time after their calculation (as indicated by the arrow between operation 325 and operation 380).

Where the devices or methods of the present invention are configured to determine a Patient Territory Digital Biomarker without further calculation of Patient Activity Factors or other consideration of patient mobility, the results of operation 320 may used in operation 350 directly (as indicated by the arrow between operation 320 and operation 350). Patient Territory Digital Biomarkers calculated in operation 350 may then be transmitted and uploaded to network-based application server 285 for storage (and possible further processing) in operation 380.

However, as discussed above, one or more Patient Activity Factors may also be calculated in order to determine an Overall Territory Activity Digital Biomarker, based upon vectors 260 calculated in operation 320. (For example, as discussed with reference to FIG. 1, Patient Activity Factors Distance, Furthest Point, and Speed may be calculated in operation 360 based on the vectors 260 and corresponding time points received from operation 320.)

In further detail, in operation 360, Patient Activity Factors (Distance, Furthest Point, Speed) may be calculated over grouped or summed intervals, taking into account assisted mobility. In some embodiments, the calculations of operation 360 may be further applied over the period of a 24-hour day (as discussed with reference to FIG. 1) in order to arrive at the Patient Activity Factors used as a basis for determining an Overall Territory Activity Digital Biomarker, as discussed with reference to FIG. 1 and Tables 1, 2A and 2B.

In operation 370, an Overall Territory Activity Digital Biomarker may be determined based upon one or more of the Patient Activity Factors and a Patient Territory Digital Biomarker determined in the previous operations, as discussed with reference to FIG. 1 and Tables 1, 2A and 2B.

In operation 380, the Overall Territory Activity Digital Biomarker determined in operation 370 may be uploaded (transmitted) to network-based application server 285 for storage in network-based storage 295 and for any further processing. Examples of further processing by the cloud-based app (e.g., network-based application 280) in operation 380 may include recalculation of Overall Territory Activity Digital Biomarkers using the digital biospecimens as a check of operations 330 through 370, or reconstruction or recalculation of the digital biomarker with a differently configured formula or algorithm (as discussed above with reference to FIG. 1).

In general, all of operations 315 through 370 may also be performed on mHealth device 210 itself prior to transmission in operation 380, which may be advantageous in order to minimize the burden on network bandwidth and to minimize storage of geolocation data on device 210. One or more of operations 330 through 370 may also be performed on a cloud-based application server after transmission of the results of operation 320, as indicated by dotted line 322.

The execution of at least operations 315 and 320 by mHealth device processor 240 are important to preserving patient locational privacy; once those operations transform otherwise personally identifiable geolocation data (e.g., GPS coordinates, etc.) into vectors (or distances and degrees), a patient is "de-located" and is no longer personally identifiable by location. Further, if the results of at least operation 320 are continuously or mostly continuously transmitted rather than stored, the loss of data if a patient's device is damaged or lost is minimized. Related, notification or reminders can be quickly sent by the device to a patient where the results of operation 320 (the digital biospecimens) by the cloud-based application server are not received as expected. Balancing considerations for the processing required for operations 330 to 370 between the patient's mHealth device and the cloud-based application may determine on which processor to execute those operations.

Aspects of the present invention may be embodied in the form of a device, a computer program product, or a method. Similarly, aspects of the present invention may be embodied as hardware, software or a combination of both. Aspects of the present invention may be embodied as a computer program product saved on one or more computer-readable media in the form of computer-readable program code embodied thereon. With regard to the configurable sampling intervals discussed herein for transforming geolocation data, an interface may be provided to mHealth-based application 250 or to network-based application 280 through network-based application server 285. The computer-readable medium may be a computer-readable signal medium or a computer-readable storage medium. A computer-readable storage medium may be, for example, an electronic, optical, magnetic, electromagnetic, infrared, or semiconductor system, apparatus, or device, or any combination thereof.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A mobile health device comprising:
    a geolocation coordinate generator for generating geolocation data and corresponding time points, the geolocation data comprising at least latitude and longitude coordinates;
    a mobile health-based application that receives the geolocation data and corresponding time points from the geolocation coordinate generator; and
    a processor that uses vector-based calculations stored in the mobile health-based application to transform the geolocation data and corresponding time points into vectors corresponding to intervals between the corresponding received time points, wherein the vectors do not contain any geolocation data, and to determine a patient territory digital biomarker based upon the vectors.

2. The device of claim 1, wherein:
    the patient territory digital biomarker and determined vectors are transmitted to a network-based application server comprising a network-based software application and a processor; and
    the network-based processor calculates one or more patient activity factors based on the vectors and further calculates an overall territory activity digital biomarker based on the one or more patient activity factors and the patient territory digital biomarker.

3. A mobile health device comprising:
    a geolocation coordinate generator for generating geolocation data and corresponding time points, the geolocation data comprising at least latitude and longitude coordinates;
    a mobile health-based application that receives the geolocation data and corresponding time points from the geolocation coordinate generator; and
    a processor that uses vector-based calculations stored in the mobile health-based application to transform the geolocation data and corresponding time points into vectors corresponding to intervals between the corresponding received time points, wherein the vectors do not contain any geolocation data, and to transmit the vectors to a network-based application server.

4. The device of claim 3, wherein the network-based application server comprises a network-based software application and a processor and wherein the application server receives the vectors, and the network processor determines a patient territory digital biomarker based on the vectors.

5. The device of claim 3, wherein the network-based application server comprises a network-based software application and a processor and wherein:
    the network-based processor determines speeds corresponding to the calculated intervals based on the determined vectors;
    the network-based processor further determines at least one starting point and one subsequent transition point based on the determined speeds;
    the network-based processor further determines indications of assisted mobility for movement between the starting point and the subsequent transition point;
    the network-based processor calculates one or more patient activity factors based on the vectors and the determined indications; and
    the network-based processor calculates on overall territory activity digital biomarker based on the one or more patient activity factors and the patient territory digital biomarker.

6. A method comprising:
    generating geolocation data and corresponding time points, wherein said geolocation data comprises at least latitude and longitude coordinates;
    transforming, using a processor and vector-based calculations stored in a mobile health-based application, the geolocation data and corresponding time points into vectors corresponding to intervals between time points corresponding to said geolocation data, wherein the vectors do not contain any geolocation data; and
    determining a patient territory digital biomarker based upon the vectors.

7. The method of claim 6, wherein the patient territory digital biomarker is determined by the processor and then is transmitted to a network-based application server.

8. The method of claim 7, further comprising:
    transmitting the vectors to the network-based application server for storage;
    calculating, using the processor, one or more patient activity factors based on the vectors;
    calculating, using the processor, an overall territory activity digital biomarker based on the one or more patient activity factors and the patient territory digital biomarker; and
    transmitting the overall territory activity digital biomarker to the network-based application server.

9. The method of claim 8, wherein said one or more patient activity factors comprise speed, overall distance and furthest point.

10. The method of claim 9, wherein said overall territory activity digital biomarker is further determined based on averages of said patient activity factors over grouped intervals.

11. The method of claim 6, wherein the vectors are transmitted to a network-based application server and the patient territory digital biomarker is determined by a processor of the network-based application server executing a network-based software application.

12. The method of claim 11, wherein:
the processor of the network-based application server:
calculates speeds corresponding to the intervals based on the determined vectors;
determines at least one starting point and one subsequent transition point based on the calculated speeds;
determines indications of assisted mobility for movement between the starting point and the subsequent transition point;
calculates one or more patient activity factors based on the vectors and the determined indications; and
calculates an overall territory activity digital biomarker based on the one or more patient activity factors and the patient territory digital biomarker; and
the overall territory activity digital biomarker is stored in the network-based application server.

13. The method of claim 12, wherein said one or more patient activity factors comprise speed, overall distance and furthest point.

14. The method of claim 13, wherein said overall territory activity digital biomarker is further determined based on averages of said patient activity factors over grouped intervals.

15. The method of claim 11, wherein:
the vectors are transmitted digital biospecimens; and
the processor of the network-based application server calculates a new patient territory digital biomarker based on the digital biospecimens, wherein the new calculation is based on a formula received from a user of said network-based software application.

* * * * *